(12) United States Patent
Heinelt et al.

(10) Patent No.: US 7,179,829 B2
(45) Date of Patent: Feb. 20, 2007

(54) SUBSTITUTED IMIDAZOLIDINES, PROCESS FOR THEIR PREPARATION, AND THEIR USE AS A MEDICAMENT OR DIAGNOSTIC, AND MEDICAMENT COMPRISING THEM

(75) Inventors: Uwe Heinelt, Wiesbaden (DE); Hans-Jochen Lang, Hofheim (DE); Armin Hofmeister, Oppenheim (DE); Klaus Wirth, Kriftel (DE)

(73) Assignee: Sanofi-aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 10/892,994

(22) Filed: Jul. 16, 2004

(65) Prior Publication Data

US 2005/0004198 A1 Jan. 6, 2005

Related U.S. Application Data

(63) Continuation of application No. 10/323,799, filed on Dec. 20, 2002, now abandoned.

(60) Provisional application No. 60/353,518, filed on Feb. 1, 2002.

(30) Foreign Application Priority Data

Dec. 21, 2001 (DE) .............................. 101 63 239

(51) Int. Cl.
*A61K 31/4168* (2006.01)
*A61K 31/4184* (2006.01)
*C07D 233/50* (2006.01)
*C07D 235/02* (2006.01)

(52) U.S. Cl. .................... 514/388; 514/392; 548/333.1; 548/302.7

(58) Field of Classification Search ............. 548/333.1, 548/302.7; 514/388, 392
See application file for complete search history.

(56) References Cited

U.S. PATENT DOCUMENTS 3,636,219 A * 1/1972 Culik et al. ................. 424/265
3,638,219 A    1/1972 Culik et al.
4,262,005 A * 4/1981 McCarthy et al. .......... 514/392
6,005,010 A   12/1999 Schwark
6,686,384 B2   2/2004 Hofmeister
6,825,231 B2  11/2004 Heinelt

FOREIGN PATENT DOCUMENTS

WO    WO 0121681    3/2001
WO    WO 0172742   10/2001
WO    WO 0179186   10/2001

OTHER PUBLICATIONS

Akhter S. et al., Squalamine, A Novel Cationic Steroid, Specifically Inhibits The Brush-Border Na+/H+ Exchanger Isoform NHE3, The American Physiological Society, 278, (Cell Physiology 45), (1999) pp. C136-C144.

Ernsberger Paul et al., Clonidine Binds To Imidazole Binding Sites As Well As alpha2-Adrenoceptors in The Ventorolateral Medulla, European Journal Of Pharmacology, 134, 1, (1987) pp. 1-13.

Fliegel Larry et al., Regulation And Characterization Of The Na+/H+ Exchanger, Biochem. Cell Biology, 76, (1998), pp. 735-741.

Jen T. et al., Amidines And Related Compounds. 6. Studies On Structure-Activity Relationships Of Antihypertensive And Antisecretory Agents Related To Clonidine, Journal of Medicinal Chemistry, 18, 1, (1976), pp. 90-99.

Ma E. et al., Expression And Localization Of Na+/H+ Exchangers In Rat Central Nervous System, Neuroscience, 79, 2, (1997), pp. 591-603.

Mohsen, et al., The Cyclodesulfurization Of Thio Compounds; VII. A New Facile Synthesis Of Na-Substituted Benzimidazoles, Synthesis Communication, Jan. 1974, S. 41-42.

Omar A-Moshen M.E. et al., The Cyclodesulfurization Of Thio Compounds; XVI Dicyclohexylcarbodiimide As An Efficient Cyclodesulfurizing Agent In The Synthesis Of Heterocyclic Compounds From Various Thio Compounds, Synthesis, 1977, pp. 864-865.

Staab Heinz A. et al., Synthese Von Isothiocyanaten, Justus Liebigs Annalen Der Chemie, 657, (1962) pp. 104-107.

Turner, et al., Transepithelial Resistance can Be Regulated by the Intestinal Brush-Border Na+/H+ Exchanger NHE3, Am. J. Physiol Cell Physiol: vol. 279; 2000; pp. 1918-1924.

Yu, et al., Functional Properties of the Rat Na/H Exchanger NHE-2 Isoform Expressed in Na/H Exchanger-deficient Chinese Hamster Ovary Cells, J. Biol. Chem.; 268; 34; 1993; pp. 25536-25541.

* cited by examiner

Primary Examiner—Laura L. Stockton
(74) Attorney, Agent, or Firm—Raymond S. Parker; Joseph D. Ross; Robert J. Kajubi

(57) ABSTRACT

The invention relates to novel compounds of the type of the imidazolidines of the formula I

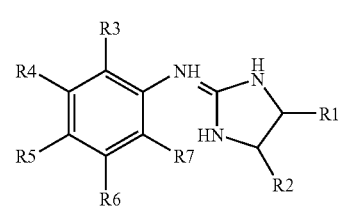

in which R1 to R7 are as defined in the claims.

They are used for preparing a medicament for the treatment or prophylaxis of the central nervous system, of lipid metabolism, of infection by ectoparasites, of disorders of gall function and for improving the respiratory drive and are therefore used for treating respiratory distress.

Additionally, the compounds increase the muscle tone of the upper respiratory tract, thus suppressing snoring.

5 Claims, No Drawings

SUBSTITUTED IMIDAZOLIDINES, PROCESS FOR THEIR PREPARATION, AND THEIR USE AS A MEDICAMENT OR DIAGNOSTIC, AND MEDICAMENT COMPRISING THEM

RELATED APPLICATIONS

This application is a continuation application of U.S. patent application Ser. No. 10/323,799, filed Dec. 20, 2002, now abandoned, which, in turn, claims the benefit of foreign priority under 35 U.S.C. § 119 of German patent application No. 10163239.8, filed on Dec. 21, 2001, the entirety of which is incorporated herein by reference. This application also claims the benefit of priority of U.S. Provisional Application No. 60/353,518, filed on Feb. 01, 2002, the contents of which are incorporated by reference herein.

The invention relates to substituted imidazolidines of the formula I,

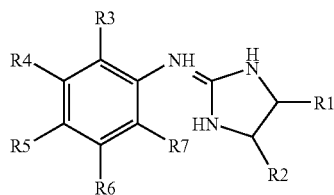

in which

R1 and R2
independently of one another are —CN, —($C_1$–$C_5$)-alkyl, —($C_2$–$C_5$)-alkenyl, —($C_2$–$C_5$)-alkynyl, —($C_3$–$C_6$)-cycloalkyl or —($C_4$–$C_6$)-cycloalkenyl
where all carbon chains and carbon rings, independently of one another, are unsubstituted or substituted by 1–11 fluorine atoms or by up to two radicals selected from the group consisting of —OH, —$NH_2$, —$NHCH_3$, —$N(CH_3)_2$ and —$OCH_3$;
or
R1 and R2
together with the two carbon atoms to which they are attached are a five- to eight-membered saturated or unsaturated carbon ring,
where the ring is unsubstituted or substituted by 1–12 fluorine atoms or by up to two radicals selected from the group consisting of —$CH_3$ and —$OCH_3$ with the proviso that there is no double bond between the two carbon atoms to which R1 and R2 are attached;
R3 is F, Cl, Br, I, —($C_1$–$C_4$)-alkyl, —($C_1$–$C_4$)-alkenyl, —($C_3$–$C_6$)-cycloalkyl, —OH, —($C_1$–$C_4$)-alkoxy, —O-phenyl, —CN, —$NO_2$ or —$NH_2$;
where the phenyl is unsubstituted or substituted by up to two radicals selected from the group consisting of $CH_3$, F, Cl, Br, I, —OH and —$OCH_3$; and
where the carbon chains or carbon rings, independently of one another, are unsubstituted or substituted by 1–11 fluorine atoms;
R4 to R6
independently of one another are H, F, Cl, Br, I, —($C_1$–$C_4$)-alkyl, —($C_1$–$C_4$)-alkenyl, —($C_3$–$C_6$)-cycloalkyl, —OH, —($C_1$–$C_4$)-alkoxy, —CN, —$NO_2$, —$NH_2$, —($C_1$–$C_4$)-alkylamino or —($C_1$–$C_4$)-dialkylamino;
where the carbon chains or carbon rings, independently of one another, are unsubstituted or substituted by 1–11 fluorine atoms;
R7 is H, F, Cl, Br, I, —($C_1$–$C_4$)-alkyl, —($C_1$–$C_4$)-alkenyl, —($C_3$–$C_6$)-cycloalkyl, —OH, —($C_1$–$C_4$)-alkoxy, —CN, —$NO_2$ or —$NH_2$;
where the carbon chains or carbon rings, independently of one another, are unsubstituted or substituted by 1–11 fluorine atoms;

and their pharmaceutically acceptable salts, and the trifluoroacetic acid salts.

In one embodiment, compounds of the formula I are chosen from
R1 and R2
independently of one another are —($C_1$–$C_5$)-alkyl, —($C_2$–$C_5$)-alkenyl, —($C_2$–$C_5$)-alkynyl, —($C_3$–$C_6$)-cycloalkyl or —($C_4$–$C_6$)-cycloalkenyl,
where all carbon chains and carbon rings, independently of one another, are unsubstituted or substituted by 1–11 fluorine atoms or by up to two radicals selected from the group consisting of —$NHCH_3$, —$N(CH_3)_2$ and —$OCH_3$;
or
R1 and R2
together with the two carbon atoms to which they are attached are a five- to eight-membered saturated or unsaturated carbon ring,
where the ring is unsubstituted or substituted by 1–12 fluorine atoms or by up to two radicals selected from the group consisting of —$CH_3$ and —$OCH_3$ with the proviso that there is no double bond between the two carbon atoms to which R1 and R2 are attached;
R3 is F, Cl, Br, I, —($C_1$–$C_4$)-alkyl, —($C_1$–$C_4$)-alkenyl, —($C_3$–$C_6$)-cycloalkyl, —OH, —($C_1$–$C_4$)-alkoxy, —O-phenyl, —CN, —$NO_2$ or —$NH_2$;
where phenyl is unsubstituted or substituted by up to two radicals selected from the group consisting of $CH_3$, F, Cl, Br, OH and $OCH_3$;
and
where the carbon chains or carbon rings, independently of one another, are unsubstituted or substituted by 1–11 fluorine atoms;
R4 to R6
independently of one another are H, F, Cl, Br, —$CH_3$, —OH, —$OCH_3$, —CN, —$NO_2$, —$NH_2$, —$NHCH_3$, or —$N(CH_3)_2$;
where the methyl group, independently of one another, are unsubstituted or substituted by 1–3 fluorine atoms;
R7 is H, F, Cl, Br, I, —($C_1$–$C_4$)-alkyl, —($C_1$–$C_4$)-alkenyl, —($C_3$–$C_6$)-cycloalkyl, —OH, —($C_1$–$C_4$)-alkoxy, —CN, —$NO_2$ or —$NH_2$;
where the carbon chains or rings, independently of one another, are unsubstituted or substituted by 1–11 fluorine atoms;

and their pharmaceutically acceptable salts, and the trifluoroacetic acid salts.

In another embodiment, compounds of the formula I are chosen from:
trans-(2-chloro-6-trifluoromethylphenyl)-(octahydrobenzimidazol-2-ylidene)amine hydrochloride,
(S,S)-(2,6-dichlorophenyl)-(octahydrobenzimidazol-2-ylidene)amine trifluoroacetic acid salt,
cis-(2,6-dichlorophenyl)-(octahydrobenzimidazol-2-ylidene)amine trifluoroacetic acid salt, (R,R)-(2,6-dichlorophenyl)-(octahydrobenzimidazol-2-ylidene)amine trifluoroacetic acid salt,
trans-(octahydrobenzimidazol-ylidene)-(2-phenoxyphenyl)amine hydrochloride,
trans-(2,6-dichlorophenyl)-(4,5-diisopropylimidazolidin-2-ylidene)amine hydrochloride,
trans-(2,6-dichlorophenyl)-(4,5-dicyclopropylimidazolidin-2-ylidene)amine trifluoracetic acid salt,
cis-(2,6-dichlorophenyl)-(4,5-dicyclopropylimidazolidin-2-ylidene)amine hydrochloride,
trans-(2,6-dichlorophenyl)-(4,5-diethylimidazolidin-2-ylidene)amine hydrochloride,
(2,6-dichlorophenyl)-(4,5-dimethylimidazolidin-2-ylidene)amine nitric acid salt,
trans-(2,6-dichlorophenyl)-(hexahydrocyclopentaimidazol-2-ylidene)amine trifluoroacetic acid salt.

In another embodiment, compounds of the formula I are chosen from:
(S,S)-(2,6-dichlorophenyl)-(octahydrobenzimidazol-2-ylidene)amine trifluoroacetic acid salt,
cis-(2,6-dichlorophenyl)-(octahydrobenzimidazol-2-ylidene)amine trifluoroacetic acid salt,
(R,R)-(2,6-dichlorophenyl)-(octahydrobenzimidazol-2-ylidene)amine trifluoroacetic acid salt,
trans-(2,6-dichlorophenyl)-(4,5-diisopropylimidazolidin-2-ylidene)amine hydrochloride,
trans-(2,6-dichlorophenyl)-(4,5-dicyclopropylimidazolidin-2-ylidene)amine trifluoroacetic acid salt,
cis-(2,6-dichlorophenyl)-(4,5-dicyclopropylimidazolidin-2-ylidene)amine hydrochloride,
trans-(2,6-dichlorophenyl)-(4,5-diethylimidazolidin-2-ylidene)amine hydrochloride,
(2,6-dichlorophenyl)-(4,5-dimethylimidazolidin-2-ylidene)amine nitric acid salt,
trans-(2,6-dichlorophenyl)-(hexahydrocyclopentaimidazol-2-ylidene)amine trifluoroacetic acid salt.

Suitable acid addition salts are salts of all pharmacologically acceptable acids, for example halides, in particular hydrochlorides, lactates, sulfates, citrates, tartrates, acetates, phosphates, methylsulfonates, p-toluenesulfonates, adipinates, fumarates, gluconates, glutamates, glycerolphosphates, maleates and pamoates. This group also corresponds to the physiologically acceptable anions; but also trifluoroacetates.

If the compounds of the formula I contain one or more centers of asymmetry, the compounds can be both S- and R-configured. The compounds can be present as optical isomers, as diastereomers, as racemates or as mixtures thereof.

The compounds of the formula I can furthermore be present as tautomers or as a mixture of tautomeric structures.

This refers in particular to the following tautomers:

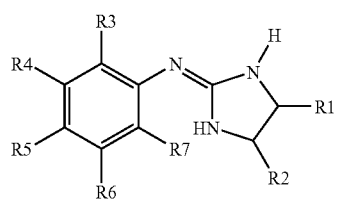

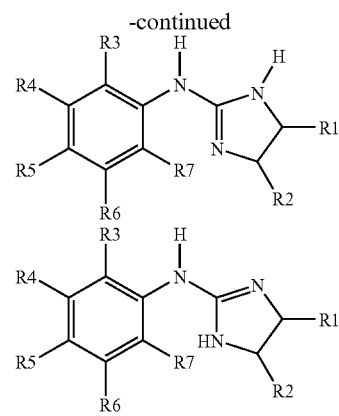

If R1 and R2 are different and if the nitrogen-carbon double bond has sufficient configurational stability, it is also possible for two double-bond isomers to exist:

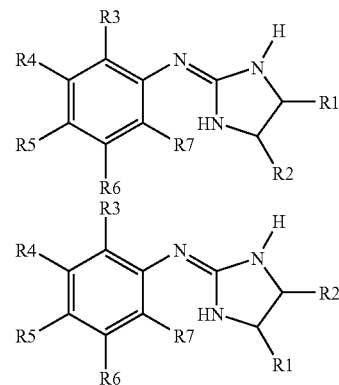

The carbon radicals mentioned, or the partially or fully fluorinated or substituted carbon radicals, can be straight-chain or branched.

Also described are methods for preparing the compounds used.

Thus, the substances described by formula I can be prepared in a manner known to the person skilled in the art from the isothiocyanate II parent compounds and the appropriate diamines III.

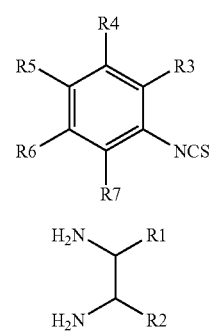

The thiourea derivative which is formed as an intermediate is cyclized using methyl iodide (Synthesis, 1974, 41–42) or carbodiimide (Synthesis, 1977, 864–865) to give the corresponding imidazolidine I. If the isothiocyanates II employed here are not commercially available, they can be prepared in a manner known from the literature from the corresponding anilines, using methods known to the person skilled in the art, for example by treatment with thiophosgene (J. Med. Chem., 1975, 18, 90–99) or thiocarbonyl diimidazole (Justus Liebigs Ann. Chem., 1962, 657, 104).

In addition to the isothiocyanates II described above, it is also possible to successfully react the isocyanates IV with amines of the type of formula III to give compounds of the formula I. Here, the urea derivative which is formed as an intermediate is cyclized using phosphorus oxychloride to give the corresponding imidazolidines of the formula I.

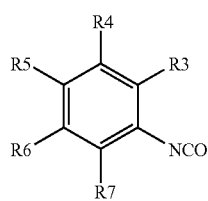

IV

In the present invention, it was surprisingly possible to demonstrate that the compounds described are potent inhibitors of the sodium/hydrogen exchanger (NHE), in particular of NHE3.

The NHE3 inhibitors known to date are derived from compounds of the acylguanidine type (EP-A 825 178, HOE 96/F226), of the norbornylamine type (DE 199 60 204.2-HMR 99/L 073), of the 2-guanidinoquinazoline type (WO 01 79 186 A1) or of the benzamidine type (WO 01 21582 A1, WO 01 72 742 A1). Squalamine, which has also been described as NHE3 inhibitor (M. Donowitz et al. Am. J. Physiol. 276 (Cell Physiol. 45): C136–C144) is, unlike the compounds of the formula I, not effective immediately but reaches its maximum potency only after one hour.

Clonidine, which is similar to the compounds described here, is known as a weak NHE inhibitor. However, its action on the NHE3 of the rat is, with an $IC_{50}$ of 620 µM, extremely moderate. In contrast, it shows a certain selectivity for the NHE2, where it has an $IC_{50}$ of 42 µM (J. Orlowski et al J. Biol. Chem. 268, 25536). It would therefore be more accurate to refer to clonidine as an NHE2 inhibitor. In addition to the weak NHE action, clonidine has a high affinity for the adrenergic alpha2 receptor and the imidazoline I1 receptor, mediating a strong hypotensive action (Ernsberger et al Eur. J. Pharmacol. 134, 1, 1987).

Compounds of the formula I have increased NHE3 activity and reduced I1 and alpha2 activity.

NHE3 is found in the body of various species, preferably in the gall bladder, the intestine and the kidney (Larry Fliegel et al, Biochem. Cell. Biol. 76: 735–741, 1998), but can also be detected in the brain (E. Ma et al. Neuroscience 79: 591–603).

Owing to this unexpected property, the compounds of formula I are suitable for treating disorders caused by oxygen deficiency. As a result of their pharmacological properties, the compounds are highly suitable for use as antiarrhythmics having a cardioprotective component, for infarct prophylaxis and infarct treatment and for treatment of angina pectoris, and they also inhibit, or strongly reduce, in a preventative manner, the pathophysiological processes which contribute to ischemically induced damage, in particular those which trigger ischemically induced cardiac arrhythmias. Owing to their protective action against pathological hypoxic and ischemic situations, the compounds of the formula I according to the invention can, as inhibitors of the cellular $Na^+/H^+$ exchange mechanisms, be used as medicaments for treating all acute or chronic damage caused by ischemia, or diseases induced primarily or secondarily by this damage. This relates to their use as medicaments for surgical interventions, for example organ transplantations, where the compounds can be used both for protecting the organs in the donor before and during removal, for protecting organs that have been removed, for example by treatment with or storage in physiological bath fluids, and also during transfer into the recipient organism. The compounds are also useful medicaments with protective action during angioplastic surgical interventions, for example at the heart, but also in peripheral vessels. Owing to their protective action against ischemically induced damage, the compounds are also suitable for use as medicaments for treating ischemias of the nervous system, in particular of the CNS, where they can be used, for example, for treating stroke or cerebral edema. Moreover, the compounds of the formula I to be used according to the invention are also suitable for treating forms of shock, such as, for example, of allergic, cardiogenic, hypovolemic and bacterial shock.

Furthermore, the compounds induce an improvement in the respiratory drive and are therefore used for the treatment of respiratory conditions in the following clinical conditions and diseases: disturbed central respiratory drive (e.g. central sleep apnea, sudden infant death, post operative hypoxia), muscular-related respiratory disorders, respiratory disorders after long-term ventilation, respiratory disorders during adaptation in a high mountain area, obstructive and mixed forms of sleep apnea, acute and chronic lung diseases with hypoxia and hypercapnia.

The compounds additionally increase the muscle tone of the upper airways, so that snoring is suppressed.

A combination of an NHE inhibitor with a carboanhydrase inhibitor (e. g. acetazolamide), the latter producing metabolic acidosis and thereby even increasing the respiratory activity, proves to be advantageous as a result of increased action and decreased use of active compound.

It has been shown that the compounds to be used according to the invention have a mild laxative action and accordingly can be used advantageously as laxatives or in the case of threatening intestinal blockage, the prevention of ischemic damage accompanying blockages in the intestinal region being particularly advantageous.

It is furthermore possible to prevent gallstone formation.

Moreover, the compounds of the formula I to be used according to the invention can exert a strong inhibitory action on the proliferation of cells, for example fibroblast cell proliferation and the proliferation of the smooth vascular muscle cells. The compounds of the formula I are therefore suitable as valuable therapeutics for diseases in which cell proliferation is a primary or secondary cause, and can therefore be used as antiatherosclerotics, agents against diabetic late complications, cancers, fibrotic disorders such as pulmonary fibrosis, liver fibrosis or kidney fibrosis, organ hypertrophy and hyperplasia, in particular in prostate hyperplasia or prostate hypertrophy.

The compounds according to the invention are effective inhibitors of the cellular sodium/proton antiporter (Na/H exchanger) which is raised in numerous disorders (essential hypertension, atherosclerosis, diabetes etc.) even in those cells which are easily accessible to measurement, such as, for example, in erythrocytes, platelets or leukocytes. The compounds to be used according to the invention are therefore suitable as outstanding and simple scientific tools, for example in their use as diagnostics for the determination and differentiation of certain forms of hypertension, but also of atherosclerosis, of diabetes, of proliferative disorders etc. Moreover, the compounds of the formula I are suitable for preventive therapy to prevent the development of high blood pressure, for example of essential hypertension.

It has moreover been found that NHE inhibitors exhibit a favorable influence on the serum lipoproteins. It is generally recognized that for the formation of artereosclerotic vascular changes, in particular of coronary heart disease, excessively high blood lipid values, 'hyperlipoproteinemias', are an essential risk factor. The lowering of increased serum lipoproteins is therefore of extreme importance for the prophylaxis and the regression of atherosclerotic changes. The compounds to be used according to the invention can therefore be used for the prophylaxis and regression of atherosclerotic changes by excluding a causal risk factor. With this protection of the vessels against the syndrome of endothelial dysfunction, compounds of the formula I are valuable pharmaceuticals for the prevention and treatment of coronary vascular spasms, of atherogenesis and of atherosclerosis, of left-ventricular hypertrophy and of dilated cardiomyopathy, and thrombotic disorders.

The compounds mentioned are therefore advantageously used for the production of a medicament for the prevention and treatment of sleep apneas and muscular-related respiratory disorders; for the production of a medicament for the prevention and treatment of snoring, for the production of a medicament for lowering the blood pressure, for the production of a medicament having laxative action for the prevention and treatment of intestinal blockages; for the production of a medicament for the prevention and treatment of disorders which are induced by ischemia and reperfusion of central and peripheral organs, such as acute kidney failure, stroke, endogenous states of shock, intestinal disorders etc; for the production of a medicament for the treatment of hypercholesterolemia; for the production of a medicament for the prevention of atherogenesis and of atherosclerosis; for the production of a medicament for the prevention and treatment of diseases which are induced by raised cholesterol levels; for the production of a medicament for the prevention and treatment of diseases which are induced by endothelial dysfunction; for the production of a medicament for the treatment of attack by ectoparasites; for the production of a medicament for the treatment of the diseases mentioned in combination with blood pressure-lowering substances, preferably with angiotensin-converting enzyme (ACE) inhibitors and angiotensin receptor antagonists. A combination of an NHE inhibitor of the formula I with an active compound lowering the blood lipid level, preferably with an HMG-CoA reductase inhibitor (e.g. lovastatin or pravastatin), the latter producing a hypolipidemic effect and thereby increasing the hypolipidemnic properties of the NHE inhibitor of the formula I, proves to be a favorable combination having intensified action and decreased use of active substance.

The administration of sodium/proton exchange inhibitors of the formula I as novel pharmaceuticals for lowering raised blood lipid levels, and the combination of sodium/proton exchange inhibitors with pharmaceuticals having a blood pressure-lowering and/or hypolipidemic action is claimed.

Pharmaceuticals which contain a compound I can in this case be administered orally, parenterally, intravenously, rectally or by inhalation, the preferred administration being dependent on the particular clinical picture of the disorder. The compounds I can in this case be used on their own or together with pharmaceutical excipients, namely both in veterinary and in human medicine.

The person skilled in the art is familiar on the basis of his/her expert knowledge with excipients which are suitable for the desired pharmaceutical formulation. In addition to solvents, gel formers, suppository bases, tablet excipients and other active compound carriers, it is possible to use, for example, antioxidants, dispersants, emulsifiers, antifoams, flavor corrigents, preservatives, solubilizers or colorants.

For a form for oral administration, the active compounds are mixed with the additives suitable therefor, such as excipients, stabilizers or inert diluents, and brought by means of the customary methods into the suitable administration forms, such as tablets, coated tablets, hard gelatin capsules, aqueous, alcoholic or oily solutions. Inert carriers which can be used are, for example, gum arabic, magnesia, magnesium carbonate, potassium phosphate, lactose, glucose or starch, in particular cornstarch. In this case, preparation can be carried out either as dry or as moist granules. Possible oily excipients or solvents are, for example, vegetable or animal oils, such as sunflower oil or cod-liver oils.

For subcutaneous or intravenous administration, the active compounds used are brought into solution, suspension or emulsion, if desired with the substances customary therefor such as solubilizers, emulsifiers or further excipients. Suitable solvents are, for example: water, physiological saline solution or alcohols, e.g. ethanol, propanol, glycerol, and in addition also sugar solutions such as glucose or mannitol solutions, or alternatively a mixture of the different solvents mentioned.

Pharmaceutical formulations suitable for administration in the form of aerosols or sprays are, for example, solutions, suspensions or emulsions of the active compound of the formula I in a pharmaceutically innocuous solvent, such as, in particular, ethanol or water, or a mixture of such solvents. If required, the formulation can also contain still other pharmaceutical excipients such as surfactants, emulsifiers and stabilizers, and a propellant. Such a preparation customarily contains the active compound in a concentration of approximately 0.1 to 10, in particular of approximately 0.3 to 3, % by weight.

The dose of the active compound of the formula I to be administered and the frequency of administration depend on the potency and duration of action of the compounds used; moreover also on the nature and severity of the disease to be treated and on the sex, age, weight and individual responsiveness of the mammal to be treated.

On average, the daily dose of a compound of the formula I in the case of a patient weighing approximately 75 kg is at least 0.001 mg/kg, preferably 0.1 mg/kg, to at most 30 mg/kg, preferably 1 mg/kg, of bodyweight. In acute episodes of the diseases, for instance, directly after a myocardial infarct, even higher and especially more frequent doses may also be necessary, e.g. up to 4 individual doses per day. In particular in the case of i.v. administration, for example in the case of an infarct patient in the intensive care unit, up to 200 mg/kg per day may be necessary.

Descriptions of the Experiments and Examples:
List of abbreviations used:
Rt retention time
TFA trifluoroacetic acid
LCMS liquid chromatography mass spectroscopy
MS mass spectroscopy
CI$^+$ chemical ionization, positive mode
ES$^+$ electrospray, positive mode General:

The retention times (Rt) stated below are based on LCMS measurements with the following parameters:

Method A:

| Stationary phase: | Merck Purospher 3μ 2 × 55 mm |
|---|---|
| Mobile phase: | 95% H$_2$O (0.05% TFA)→ 95% acetonitrile; 4 min; 95% acetonitrile; 1.5 min → 5% acetonitrile; 1 min; 0.5 ml/min. |

Method B:

| Stationary phase: | YMC J'sphereODS H80 2 × 33 mm |
|---|---|
| Mobile phase: | 95% H$_2$O (0.05% TFA)→ 95% acetonitrile; 2.3 min; 95% acetonitrile; 1 min → 5% acetonitrile; 0.1 min: 1 ml/min. |

Preparative HPLC was carried out under the following conditions:

| Stationary phase: | Merck Purospher RP18 (10 μM) 250 × 25 mm |
|---|---|
| Mobile phase: | 90% H$_2$O (0.05% TFA)→ 90% acetonitrile; 40 min; 25 ml/min |

If the compounds are enantiomerically pure, the configuration and/or the sign of the optical rotation is given. If these data are missing, the compounds are racemates or not optically active.

EXAMPLE 1

(S,S)-(2,6-Dichlorophenyl)-(octahydrobenzimidazol-2-ylidene)amine trifluoroacetic acid salt

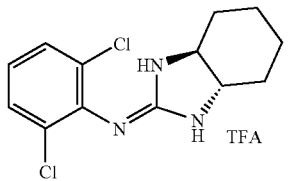

2,6-Dichlorophenyl isothiocyanate (600 mg) and (1S,2S)-(+)-1,2-diaminocyclohexane (336 mg) were dissolved in toluene (30 ml) and stirred at 70° C. for 3 h. The mixture was allowed to stand overnight and the solvent was then removed under reduced pressure, and ether was added to the residue. The resulting thiourea was then filtered off with suction. 840 mg of the desired product were isolated.

A fraction of the thiourea obtained in this manner (420 mg) was then admixed with toluene (15 ml) and briefly heated at reflux. N,N'-Dicyclohexylcarbodiimide (226 mg), dissolved in toluene (5 ml), was then added dropwise, and the mixture was stirred at 70° C. for 5 h. The mixture was allowed to stand overnight and the resulting precipitate was then filtered off and the filtrate was concentrated to dryness. The residue was then purified by preparative HPLC. The pure fractions were combined, the acetonitrile was removed using a rotary evaporator and the aqueous phase was freeze-dried. This gave 70 mg of the desired compound.

LCMS-Rt: 3.69 min, (A)
MS (ES$^+$, M+H$^+$): 284.2

EXAMPLE 2 cis-(2,6-Dichlorophenyl)-(octahydrobenzimidazol-2-ylidene)amine trifluoroacetic acid salt

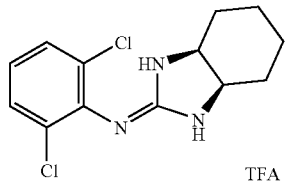

2,6-Dichlorophenyl isothiocyanate (600 mg) and cis-1,2-diaminocyclohexane (336 mg) were reacted and worked up as described in Example 1. From the 900 mg of thiourea obtained in the first step, 454 mg were reacted further in the next step. This gave 112 mg of the desired compound.

LCMS-Rt: 3.65 min, (A)
MS (CI$^+$, M+H$^+$): 284.1

EXAMPLE 3

(R,R)-(2,6-Dichlorophenyl)-(octahydrobenzimidazol-2-ylidene)amine trifluoroacetic acid salt

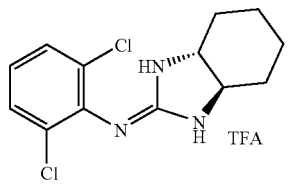

2,6-Dichlorophenyl isothiocyanate (50 mg) and (R,R)-(−)-1,2-diaminocyclohexane (28 mg) were initially charged in toluene (1.5 ml) and heated at reflux for 15 min. N,N'-Dicyclohexylcarbodiimide (76 mg) was then added, and the mixture was kept further at reflux. The mixture was allowed to stand overnight and the toluene was then removed and the residue was purified by preparative HPLC. Since the first purification gave only contaminated fractions, chromatography was repeated using a different column (MN Nucleosil 100-5-C18 250×25 mm; flow rate 20 ml/min), but with otherwise identical conditions. The pure fractions were combined, the acetonitrile was removed using a rotary evaporator and the aqueous phase was freeze-dried. This gave 10 mg of the desired compound.

LCMS-Rt: 3.70 min, (A)
MS (CI$^+$, M+H$^+$): 284.0

EXAMPLE 4 trans-(Octahydrobenzoimidazol-2-ylidene)-(2-phenoxyphenyl)amine hydrochloride

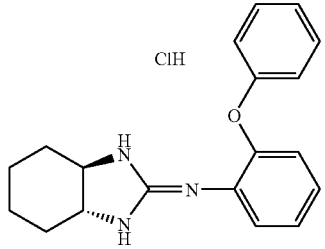

a) 2-Phenoxyphenyl isothiocyanate
1.96 g (0.011 mol) of thiocarbonyl diimidazole were added to a solution of 1.85 g (0.01 mol) of 2-phenoxyaniline in 50 ml of THF and the mixture was stirred at room temperature for 4 hours, giving, after removal of the solvent by distillation, the compound as a brown amorphous product.

b) N-(trans-2-Aminocyclohexyl)-N'-(2-phenoxyphenyl)thiourea

A solution of 1.6 g of 2-phenoxyphenyl isothiocyanate in 10 ml of THF was added to a solution of 0.8 g of trans-1,2-diaminocyclohexane in 30 ml of THF, and the mixture was stirred at room temperature for about 4 hours. The solvent was evaporated and the residue was subsequently subjected to column chromatography on silica gel using a mixture of 10 parts of ethyl acetate, 5 parts of n-heptane, 5 parts of methylene chloride, 5 parts of methanol and 1 part of concentrated aqueous ammonia solution, giving the desired compound as an amorphous oily product.

c) trans-(Octahydrobenzimidazol-2-ylidene)-(2-phenoxyphenyl)amine hydrochloride 3.4 g of methyl iodide were added to a solution of 1.03 g of N-(trans-2-aminocyclohexyl)-N'-(2-phenoxyphenyl)thiourea in 30 ml of ethanol, and the reaction mixture was kept at reflux for 5 hours. The mixture was allowed to stand overnight and the solvent was then distilled off and the residue was treated with water and subsequently made alkaline using saturated sodium bicarbonate solution. The aqueous phase was extracted with ethyl acetate and the organic extraction phase was evaporated, and the oily residue was then chromatographed on silica gel using a mixture of 10 parts of ethyl acetate, 5 parts of n-heptane, 5 parts of methylene chloride, 5 parts of methanol and 1 part of concentrated aqueous ammonia solution. This gave an oily product which was dissolved in ethyl acetate and acidified using a saturated solution of HCl gas in diethyl ether. The solvent was distilled off and the residue was then dissolved in water and subjected to freeze-drying. This gave 0.49 g of a solid of m.p. 110° C.

MS (ES$^+$, M+H$^+$): 308.2

EXAMPLE 5 trans-(2-Chloro-6-trifluoromethylphenyl)-(octahydrobenzimidazol-2-ylidene)amine hydrochloride

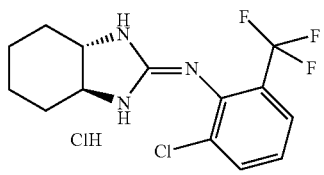

a) N-(trans-2-Aminocyclohexyl)-N'-(2-chloro-6-trifluoromethylphenyl)urea

A solution of 0.46 g of trans-1,2-diaminocyclohexane in 10 ml of THF was added to a solution of 1.6 g of 2-chloro-6-trifluoromethylphenyl isocyanate in 30 ml of THF, and the mixture was stirred at room temperature for about 3 hours. The mixture was allowed to stand overnight and the solvent was then distilled off, giving 0.57 g of the desired compound as a semi-solid yellow product.

b) trans-(2-Chloro-6-trifluoromethylphenyl)-(octahydrobenzimidazol-2-ylidene)amine hydrochloride 0.57 g of N-(trans-2-aminocyclohexyl)-N'-(2-chloro-6-trifluoromethylphenyl)urea in 20 ml of phosphorus oxychloride (POCl$_3$) was boiled at reflux for 4–5 hours. The POCl$_3$ was distilled off, water was added to the residue and the pH was adjusted to 7–8 using 2N NaOH. The mixture was then extracted with ethyl acetate, the organic solvent was distilled off and the residue was chromatographed on silica gel using a mixture of 20 parts of ethyl acetate, 10 parts of n-heptane and 3 parts of glacial acetic acid. After removal of the eluent by distillation, the white solid residue was dissolved in a little ethyl acetate and acidified using a saturated solution of HCl gas in diethyl ether. Removal of the solvent by distillation and treatment of the residue with diisopropyl ether gave 0.4 g of the desired product as a solid of m.p. 160–165° C.

MS (CI$^+$, M+H$^+$): 318.3

EXAMPLE 6 trans-(4,5-Di-tert-butylimidazolidin-2-ylidene)-(2,6-dichlorophenyl)amine hydrochloride

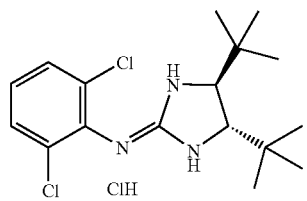

2,6-Dichlorophenyl isothiocyanate (150 mg) and trans-2,2,5,5-tetramethylhexane-3,4-diamine (127 mg)—analogously to Synthesis 1999, 2, 228; in racemic form—were initially charged in toluene (1.5 ml) and heated at reflux for 15 min. N,N'-Dicyclohexylcarbodiimide (126 mg), dissolved in 2 ml of toluene, was then added, and the mixture was kept at reflux. After standing overnight, the toluene was removed under reduced pressure and the residue was purified by preparative HPLC. The pure fractions were combined, the acetonitrile was removed using a rotary evaporator and the aqueous phase was neutralized with saturated potassium carbonate solution and extracted three times with ethyl acetate. The combined ethyl acetate phases were washed with saturated sodium chloride solution and then dried over magnesium sulfate. The drying agent was filtered off, the mixture was concentrated and the residue was then taken up in water, 2N hydrochloric acid was added and the mixture was freeze-dried. This gave 111 mg of the desired compound.

LCMS-Rt: 4.43 min, (A)

MS (CI$^+$, M+H$^+$): 342.2

EXAMPLE 7 trans-(2,6-Dichlorophenyl)-(4,5-diisopropylimidazolidin-2-ylidene)amine hydrochloride

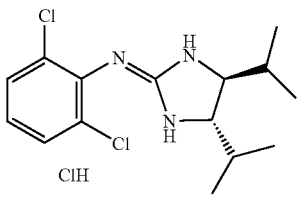

trans-2,5-Dimethylhexane-3,4-diamine (226 mg)—analogously to Synthesis 1999, 2, 228; in racemic form—was initially charged in THF (2.5 ml), and 2,6-dichlorophenyl isothiocyanate was added a little at a time (portions of 150, 80 and 40 mg) at room temperature. N,N'-Dicyclohexylcarbodiimide (324 mg) was then added, and the mixture was further stirred at room temperature. To complete the reaction, some more N,N'-dicyclohexylcarbodiimide was added. The mixture was allowed to stand overnight, and the resulting precipitate was then filtered off with suction and the filtrate was concentrated. The residue was purified by preparative HPLC. The pure fractions were combined, the acetonitrile was removed using a rotary evaporator and the aqueous phase was neutralized with saturated potassium carbonate solution and extracted three times with ethyl acetate. The combined ethyl acetate phases were washed with saturated sodium chloride solution and then dried over magnesium sulfate. The drying agent was filtered off and the mixture was concentrated, and the residue was then taken up in water, 2N hydrochloric acid was added and the mixture was freeze-dried. This gave 220 mg of the desired compound.

LCMS-Rt: 1.93 min, (B)

MS (ES$^+$, M+H$^+$): 314.1

The compounds described in the table below were synthesized according to the examples stated in each case:

| Example | | Salt | Analogously to Example | MS [M+H$^+$] | LCMS-Rt [min] |
|---------|---|------|------------------------|--------------|----------------|
| 8 | 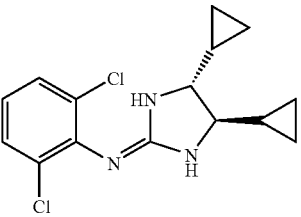 | TFA | 7 | 309.0(ES$^+$) | 1.84(B) |
| 9 | 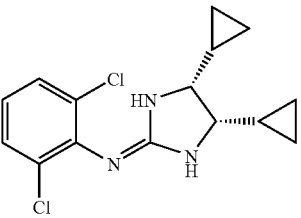 | HCl | 7 | 309.1(ES$^+$) | 1.87(B) |
| 10 | 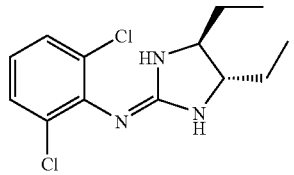 | HCl | 7 | 286.1(ES$^+$) | 1.75(B) |
| 11 | 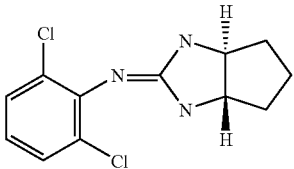 | TFA | 7 | 270.1(ES$^+$) | 1.56(B) |
| 12 | 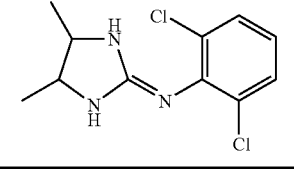 | HNO$_3$ | | | |

Pharmacological Data:

Test Description:

In this test, the recovery of the intracellular pH ($pH_i$) after an acidification, which starts when the NHE is capable of functioning, even under bicarbonate-free conditions, was determined. For this purpose, the $pH_i$ was determined using the pH-sensitive fluorescent dye BCECF (calbiochem, the precursor BCECF-AM is employed). The cells were initially loaded with BCECF. The BCECF fluorescence was determined in a "ratio fluorescence spectrometer" (Photon Technology International, South Brunswick, N.J., USA) with excitation wavelengths of 505 and 440 nm and an emission wavelength of 535 nm, and was converted into the $pH_i$ using calibration plots. The cells were incubated in $NH_4Cl$ buffer (pH 7.4) ($NH_4Cl$ buffer: 115 mM NaCl, 20 mM $NH_4Cl$, 5 mM KCl, 1 mM $CaCl_2$, 1 mM $MgSO_4$, 20 mM Hepes, 5 mM glucose, 1 mg/ml BSA; a pH of 7.4 is established with 1 M NaOH) even during the BCECF loading. The intracellular acidification was induced by addition of 975 μl of an $NH_4Cl$-free buffer (see below) to 25 μl aliquots of the cells incubated in $NH_4Cl$ buffer. The subsequent rate of pH recovery was recorded in the case of NHE1 for two minutes, in the case of NHE2 for five minutes and in the case of NHE3 for three minutes. To calculate the inhibitory power of the tested substances, the cells were initially investigated in buffers in which complete or absolutely no pH recovery took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM Hepes, 5 mM glucose, a pH of 7.0 is established with 1 M NaOH). To determine the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_4$, 0.23 mM $KH_2PO_4$, 5 mM Hepes, 5 mM glucose, a pH of 7.0 is established with 1 M KOH). The substances to be tested were made up in the $Na^+$-containing buffer. Recovery of the intracellular pH at the tested concentration of a substance was expressed as a percentage of the maximum recovery. Using the Sigma-Plot program, the $IC_{50}$ value of the substance in question was calculated for the individual NHE subtypes using the percentages for pH recovery.

| Example | $IC_{50}$ [μM], (rNHE3) |
|---|---|
| 5 | 19 |
| 7 | 1.1 |
| 12 | ~3 |

What is claimed is:

1. An imidazlidine of the formula

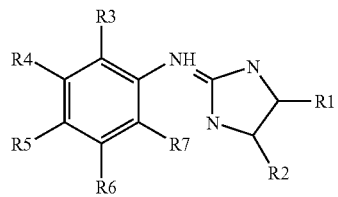

in which

R1 and R2
  independently of one another are —CN, —($C_2$–$C_5$)-alkyl, —($C_2$–$C_5$)-alkenyl, —($C_2$–$C_5$)-alkynyl, —($C_3$–$C_6$)-cycloalkyl or —($C_4$–$C_6$)-cycloalkenyl where the carbon chains and carbon rings, independently of one another, are unsubstituted or substituted by 1–11 fluorine atoms or by up to two radicals selected from the group consisting of —OH; —$NH_2$, —$NHCH_3$, —$N(CH_3)_2$ and —$OCH_3$;

or

R1 and R2
  together with the two carbon atoms to which they are attached arc a five-to eight-membered, non-aromatic, saturated or unsaturated carbon ring, where the ring is unsubstituted or substituted by 1–12 fluorine atoms or by up to two radicals seleced from the group consisting of —$CH_3$ and —$OCH_3$, with the proviso that there is no double bond between the two carbon atoms to which R1 and R2 are attached;

R3 is F, Cl, Br, I, —($C_1$–$C_4$)-alkYl, —($C_2$–$C_4$)-alkenyl, —($C_3$–$C_6$)-cycloalkenyl, —OH, —($C_1$–$C_4$)-alkoxy, —O-phenyl, —CN, —$NO_2$ or —$NH_2$;
  where the phenyl is unsubstituted or substituted by up to two radicals selected from the group consisting of —$CH_3$, F, Cl, Br, I, —OH and —$OCH_3$; and
  where the carbon chains or carbon rings, independently of one another, are unsubstituted or substituted by 1–11 fluorine atoms;

R4 to R6
  independently of one another are H, F, Cl, Br, I, —($C_2$–$C_4$)-alkyl, —($C_2$–$C_4$)-alkenyl, —($C_3$–$C_6$)-cycloalkyl, —OH, —($C_1$–$C_4$)-alkoxy, —CN, —$NO_2$, —$NH_2$, —($C_1$–$C_4$)-alkylamino or —($C_1$–$C_4$)-dialkylamino;
  where the carbon chains or carbon rings, independently of one another, are unsubstituted or substituted by 1–11 fluorine atoms;

R7 is H, F, Cl, Br, I, —($C_1$–$C_4$)-alkyl, —($C_2$–$C_4$)-alkenyl, —($C_3$–$C_6$)-cycloalkyl, —OH, —($C_1$–$C_4$)-alkoxy, —CN, —$NO_2$ or $NH_2$;
  where the carbon chains or carbon rings independently of one another, are unsubstituted or substituted by 1–11 fluorine atoms;

or a pharmaceutically acceptable, salt thereof, or a trifluoroacetic acid salt thereof, in any stereoisomeric form, or a mixture of any such compounds in any ratio.

2. The compound as claimed in claim 1, in which

R1 and R2
  independently of one another are —($C_1$–$C_5$)-alkyl, —($C_2$–$C_5$)-alkenyl, —($C_2$–$C_5$)-alkynyl, —($C_3$–$C_6$)-cycloalkyl or —($C_4$–$C_6$)-cycloalkeyl,
  where the carbon chains and carbon rings, independently of one another, are unsubstituted or substituted by 1–11 fluorine atoms or by up to two radicals selected from the group consisting of —$NHCH_3$, —$N(CH_3)_2$ and —$OCH_3$;

or

R1 and R2
  together with the two carbon atoms to which they are attached are a five-to eight-membered, non-aromatic, saturated or unsaturated carbon ring, where the ring is unsubstituted or substituted by 1–12 fluorine atoms or by up to two radicals selected from the group consisting of —$CH_3$ and —$OCH_5$;
  with the proviso that there is no double bond between the two carbon atoms to which R1 and R2 are attached;

R3 is F, Cl, Br, I, —($C_1$–$C_4$)-alkyl, —($C_2$–$C_4$)-alkenyl, —($C_3$–$C_6$)-cycloalkyl, —OH, —(C1.C4)-alkoxy, —O-phenyl, —CN, —$NO_2$ or —$NH_2$;

where the phenyl is unsubstituted or substituted by up to two radicals selected from the group consisting of —CH$_3$, F, Cl, BR, —OH and —OCH$_3$; and where the carbon chains or carbon rings independently of one another, are unsubstituted or substituted by 1–11 fluorine atoms;

R4 to R6 independently of one another are H, F, Cl, Br, —CH$_3$, —OH, —OCH$_3$, —CN, —NO$_2$, —NH$_2$, —NHCH$_3$, or —N(CH$_3$)$_2$;

where the methyl group, independently of one another, are unsubstituted or substituted by 1–3 fluorine atoms;

R7 is H, F, Cl, Br, I, —(C$_1$–C$_4$)-alkyl, —(C$_2$–C$_4$)-alkenyl, —(C$_3$–C$_6$)-cycloalkyl, —OH, —(C$_1$–C$_4$)-alkoxy, —CN, —NO$_2$ or —NH$_2$;

where the carbon chains or carbon rings, independently of one another, are unsubstituted or substituted by 1–11 fluorine atoms;

or a pharmaceutically acceptable salt thereof, or a trifluoroacetic acid salt thereof, in any stereoisomeric form, or a mixture of any such compounds in any ratio.

3. The compound as claimed in claim 1, chosen from:
trans-(2-chloro-6-trifluoromethylphenyl)-(octahydrobenzimidazol-2-ylidene)amine hydrochloride,
(S,S)-(2,6-dichlorophenyl)-(octahydrobenzimidazol-2-ylidene)amine trifluoroacetic acid salt,
cis-(2,6-dichlorophenyl)-(octahydrobenzimidazol-2-ylidene)amine trifluoroacetic acid salt,
(R,R)-(2,6-dichlorophenyl)-(octahydrobenzimidazol-2-ylidene)amine trifluoroacetic acid salt,
trans-(octahydrobenzimidazol-2-ylidene)-(2-phenoxyphenyl)amine hydrochloride,
trans-(2,6-dichlorophenyl)-(4,5-diisopropylimidazolidin-2-ylidene)amine hydrochloride,
trans-(2,6-dichlorophenyl)-(4,5-dicyclopropylimidazolidin-2-ylidene)amine trifluoroacetic acid salt,
cis-(2,6-dichlorophenyl)-(4,5-dicyclopropylimidazolidin-2-ylidene)amine hydrochloride,
trans-(2,6-dichlorophenyl)-(4,5-diethylimidazolidin-2-ylidene)amine hydrochloride,
(2,6-dichlorophenyl)-(4,5-diimethylimidazolidin-2-ylidene)amine nitric acid salt, and
trans-(2,6-dichlorophenyl)-(hexahydrocyclopentaimidazol-2-ylidene)amine trifluoroacetic acid salt.

4. The compound as claims in claim 1, chosen from:
(S,S)-(2,6-dichlorophenyl)-(octahydrobenzimidazol-2-ylidene)amine trifluoroacetic acid salt,
cis-(2,6-dichlorophenyl)-(octahydrobenzimidazol-2-ylidene)amine trifluoroacetic acid salt,
(R,R)-(2,6-dichlorophenyl)-(octahydrobenzimidazol-2-ylidene)amine trifluoroacetic acid salt,
trans-(2,6-dichlorophenyl)-(4,5-diisopropylimidazolidin-2-ylidene)amine hydrochloride,
trans-(2,6-dichlorophenyl)-(4,5-dicyclopropylimidazolidin-2-ylidene)amine trifluoroacetic acid salt,
cis-(2,6-dichlorophenyl)-(4,5-dicyclopropylimidazolidin-2-ylidene)amine hydrochloride,
trans-(2,6-dichlorophenyl)-(4,5-diethylimidazolidin-2-ylidene)amine hydrochloride,
(2,6-dichlorophenyl)-(4,5-dimethylimidazolidin-2-ylidene)amine nitric acid salt, and
trans-(2,6-dichlorophenyl)-(hexahydrocyclopentaimidazol-2-ylidene)amine trifluoroacetic acid salt.

5. A pharmaceutical comprising at least one compound as claimed in claim 1 and at least one pharmaceutical carrier, with the proviso that said compound is not a trifluoroacetic acid salt.

* * * * *

UNITED STATES PATENT AND TRADEMARK OFFICE
CERTIFICATE OF CORRECTION

PATENT NO. : 7,179,829 B2
APPLICATION NO. : 10/892994
DATED : February 20, 2007
INVENTOR(S) : Heinelt et al.

Page 1 of 1

It is certified that error appears in the above-identified patent and that said Letters Patent is hereby corrected as shown below:

Column 15:
In claim 1, line 55 after "formula" kindly delete the structure

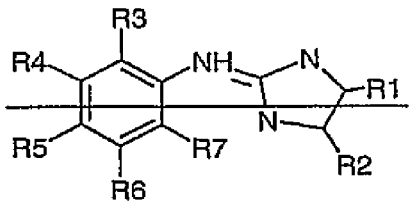

And insert therefore:

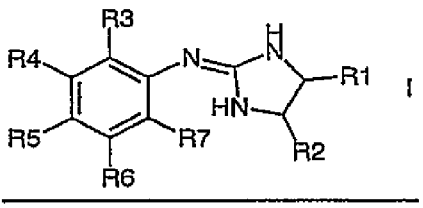

Signed and Sealed this

Twenty-sixth Day of June, 2007

JON W. DUDAS
*Director of the United States Patent and Trademark Office*